United States Patent [19]
Hsi

[11] Patent Number: 5,393,979
[45] Date of Patent: Feb. 28, 1995

[54] PHOTO-IONIZATION DETECTOR FOR DETECTING VOLATILE ORGANIC GASES

[75] Inventor: Peter C. Hsi, Alameda County, Calif.
[73] Assignee: RAE Systems, Inc., Sunnyvale, Calif.
[21] Appl. No.: 61,418
[22] Filed: May 12, 1993
[51] Int. Cl.⁶ .............................................. G01N 27/66
[52] U.S. Cl. ..................................... 250/382; 250/379; 250/423 P; 324/464
[58] Field of Search .................... 250/423 P, 382, 379; 324/464, 465

[56] References Cited

U.S. PATENT DOCUMENTS 2,959,677 11/1960 Robinson et al. ................... 250/382
5,254,861 10/1993 Carpenter et al. .................. 250/379

*Primary Examiner*—Carolyn E. Fields
*Attorney, Agent, or Firm*—Flehr, Hohbach, Test, Albritton & Herbert

[57] ABSTRACT

A photo-ionization detector utilizes an ultraviolet (UV) lamp for detecting and measuring the concentration of volatile gases flowing between closely spaced parallel electrodes. One of the electrodes is made of mesh to allow photons to pass into the space between the electrodes to ionize the volatile gases between the electrodes. The detector also incorporates an improved ionization chamber. In other embodiments, a plurality of gas discharge lamps, each generating a different photon energy, may be placed adjacent to a plurality of closely spaced electrodes, all electrodes in one ionization chamber, to detect and measure different types of volatile gases that may exist.

14 Claims, 2 Drawing Sheets

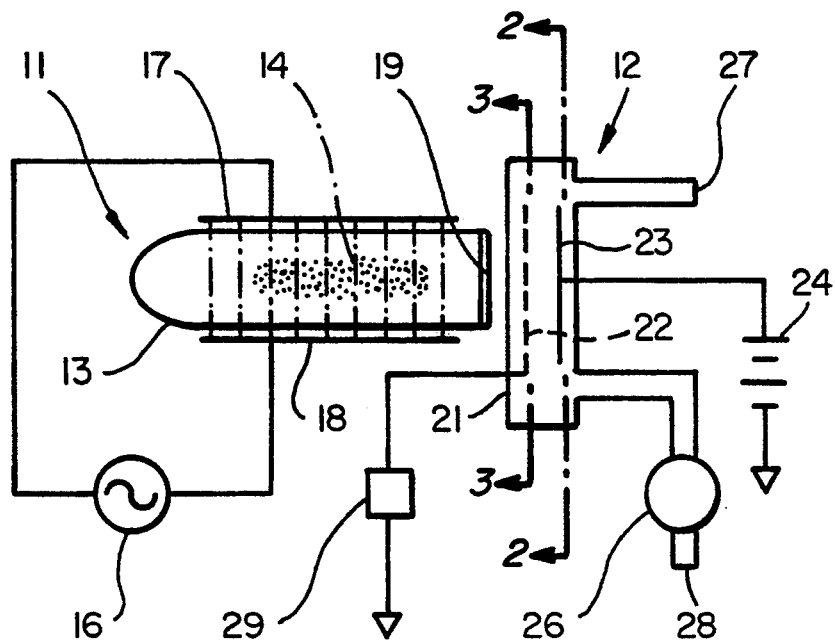
FIG_1
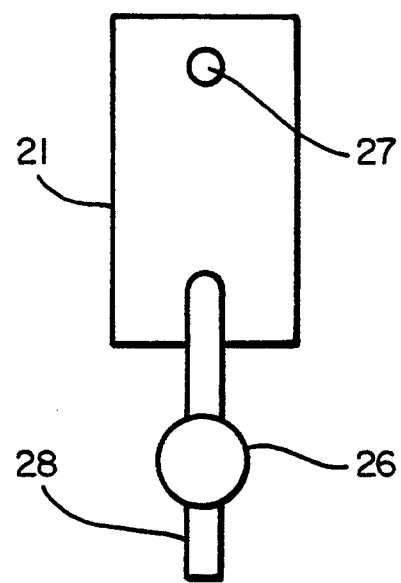
FIG_2

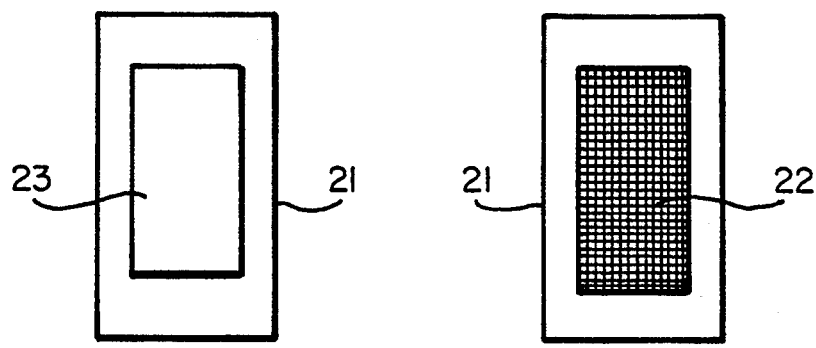
FIG_3  FIG_4
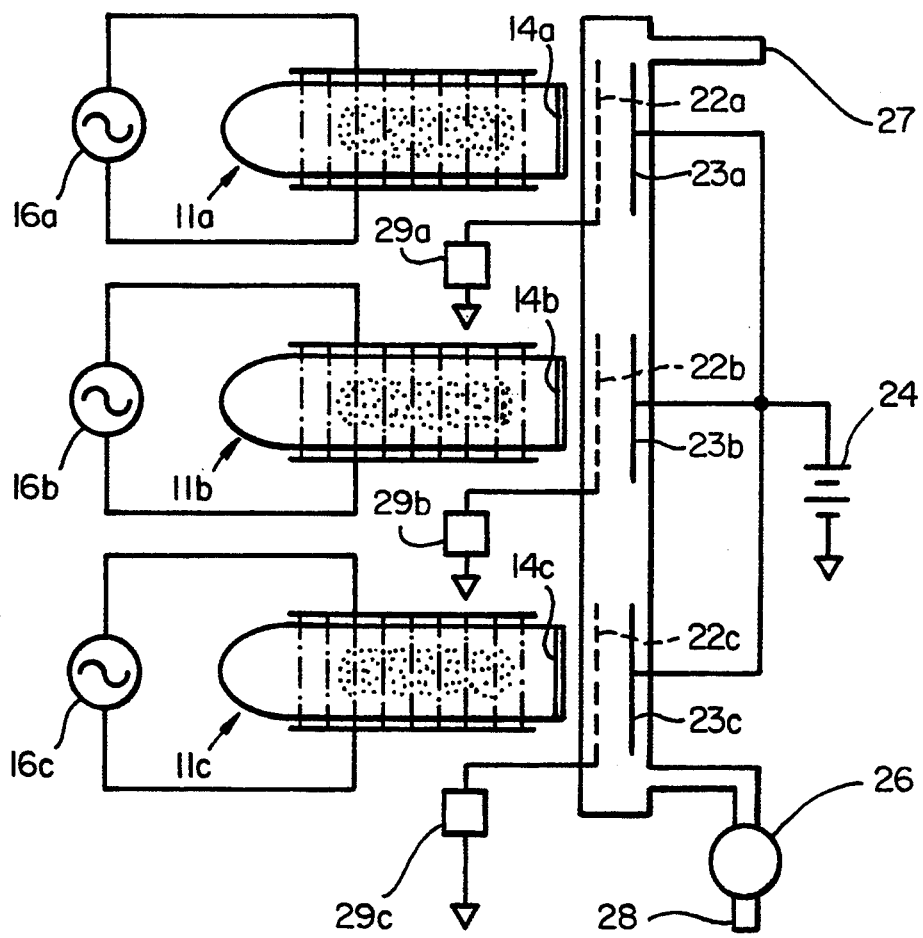
FIG_5

PHOTO-IONIZATION DETECTOR FOR DETECTING VOLATILE ORGANIC GASES

BRIEF DESCRIPTION OF THE INVENTION

This invention relates generally to a photo-ionization detector for detecting and measuring the concentration of volatile organic gases, and more particularly to a photo-ionization detector having an improved ionization chamber and novel gas discharge UV lamp.

BACKGROUND OF THE INVENTION

Photo-ionization detection (PID) is a well-established method to detect volatile organic gas. The basic design of PID detectors includes a high-energy photon source, an ionization chamber, and a pair of electrodes. Typically, a gas discharge ultraviolet (UV) lamp is used as the high-energy photon source. This lamp produces photons with photon energy of 9.2 eV and above. When such high-energy photons hit organic gas molecules, molecules having ionization levels below the photon energy are ionized. In most PID instrument designs, the organic gas is brought into an ionization chamber by a pump. A UV lamp illuminates the chamber with high-energy photons. The resulting ions will cause a current flow between two electrodes disposed inside the chamber. An electrometer is used to measure the current. The current measurement can be converted into concentration in parts per million (ppm) of the organic gas based on the flow rate of the gas stream.

In a classical PID design, a glow discharge UV lamp is used to produce high-energy photons. The lamp is constructed with two electrodes placed inside a sealed glass envelope. The glass envelope is filled with certain gases, such as helium, argon or krypton. High voltage is applied between the two electrodes to induce an ionization process (i.e., separation of the electrons from the molecules). The ions and electrons are recombined shortly after to generate photons. These photons then pass through a UV window in the glass envelope to illuminate an associated ionization chamber.

A classical ionization chamber is constructed with an airtight housing and a pair of closely-spaced electrodes. The gas is introduced to the chamber through a small gas inlet and leaves the chamber through a gas outlet. The two electrodes are generally arranged in concentric form with one electrode in the middle of a cylindrical shaped electrode. A high-voltage DC (>150 V) is applied between the two electrodes to generate a high electric field. The UV window of the lamp is placed directly over the space between the two electrodes. When the gas molecules enter the chamber, they are ionized by the photons from the UV lamp. The resulting ions and electrons will be attracted to the two electrodes by the electric field. An electrometer measures the current flow.

The ionization chamber of the prior art has several disadvantages. The distance from the center electrode to the outside cylindrical electrode is relatively large (about the radius of the UV window). In order to achieve high electric field strength, relatively high voltage needs to be applied between the two electrodes. In addition, because of the long distance between the two electrodes, some ions and electrons will recombine before they reach the electrodes. As a result, the sensitivity of the detector is reduced. Once leaving the UV window of the lamp, the high energy photons travel a very short distance before they are absorbed by the organic gas molecules. Therefore, the region that photo-ionization process actually take place is just a few millimeters in front of the UV window. Beyond that region, the photo-ionization activity decreases rapidly. Therefore, in a classical cylindrical chamber design, the effective region for photo-ionization is limited only to the space right in front of the UV window. The gas molecules far from the UV window are unlikely to be ionized.

The prior art UV lamps, although useful in connection with the novel chamber of this invention, also have certain drawbacks, such as short life and low efficiency. In my co-pending application, Ser. No. 08/061,419, filed simultaneously herewith, there is described a novel gas discharge UV lamp particularly suitable for use in the photo-ionization detector of this invention.

The basic prior art photo-ionization detector has an inherent limitation: it cannot distinguish between different gases with similar ionization energy. When the high-energy photon hits a gas molecule, if the photon energy is higher than the ionization energy of the molecule, it will ionize it. By measuring the amount of ions and comparing it with a pre-defined reference value for that gas, the gas concentration can be calculated. However, there is usually more than one type of gas which has lower ionization energy than a specific photon energy. Therefore, for a given photon energy, these gas molecules can all be ionized. It is not possible to identify a specific gas and its correct concentration if the type of gas is unknown. In addition, if there is more than one type of gas present at the same time and the photon energy is higher than the ionization energy of these gases, it is also not possible to calculate the correct concentration of each individual gas.

This lack of specificity is a major drawback of present day PID instruments. They can be used to detect a single gas type. However, the user needs to know ahead of time what type of gas is being measured, and set the instrument calibration accordingly. Traditionally, a separation column is placed in front of the PID in order to separate the gas molecules before they enter the PID for detection and measurements.

The two most critical elements in the PID instrument design are the high-energy UV light source and the ionization chamber. A good UV light source produces stable UV light output and is very reliable and rugged. It also needs to be energy efficient, if it is to be used in portable battery-powered instruments. The chamber should be designed in such a way that even a very small number of gas molecules (less than one part per million) can be measured accurately. The instrument should be capable of distinguishing the type of gas.

OBJECTS AND SUMMARY OF THE INVENTION

It is a general object of this invention to provide a detector for detecting volatile gases.

It is another object of the invention to provide a volatile gas detector capable of detecting multiple volatile gases.

It is another object of the invention to provide a volatile gas detector which is efficient and simple in construction.

The foregoing and other objects of the invention are achieved by a detector that includes closely-spaced parallel electrodes for detecting the ionization of volatile gases flowing past electrodes by photons from a UV lamp.

BRIEF DESCRIPTION OF THE DRAWINGS

The foregoing and other objects will be more clearly understood by reading the accompanying description and the drawings, of which:

FIG. 1 shows a photo-ionization detector in accordance with one embodiment of the invention;

FIG. 2 is a rear elevational view of the photo-ionization detector of FIG. 1;

FIG. 3 is a sectional view taken along the line 2—2 of FIG. 1;

FIG. 4 is a sectional view taken along the line 3—3 of FIG. 1; and

FIG. 5 shows a photo-ionization detector in accordance with another embodiment of the invention.

DESCRIPTION OF PREFERRED EMBODIMENTS(s)

The photo-ionization detector assembly, FIG. 1, includes a UV lamp 11 which radiates photons that enter an ionization chamber 12 to ionize volatile gas molecules in the chamber.

The UV lamp is of the type described in detail in my co-pending application, Ser. No. 08/061,419, filed herewith. For sake of completeness, the lamp will be briefly described. The lamp includes an envelope 13 which contains a mixture of gases such as helium, argon and hydrogen which can be ionized by an electric field to form electrons and ions which recombine to generate photons. For example, the gas mixture may be 30% helium, 30% argon and 40% hydrogen at a pressure of 10 Torr.

The gas molecules are ionized by an electric field 14 provided by applying a high AC voltage 16 to the spaced plates 17 and 18. For example, the voltage may be selected to provide a live electric field having an intensity of between 650 and 1250 volts at a frequency of between 40 and 100 kHz. A window 19 is formed at one end of the envelope and is selected to pass photons having predetermined energies.

The ionization chamber for the PID is a small cavity 21 of a few millimeters in thickness disposed in front of the UV window 19 of the lamp 11. In one embodiment, the separation between the two electrodes 22, 23 is between 0.020 to 0.040 inch, inclusive. Two parallel electrodes 22, 23 are placed very close to each other inside this cavity. A high DC voltage 24 is applied between these two electrodes. In an enlarged rear elevation view of the PID, FIG. 2 shows the small gas inlet 27, pump 26, and a gas outlet 28. The gas is sucked into the chamber by a pump 26 through a small gas inlet 27. The gas is forced to pass through the cavity as a thin sheet of gas between the two electrodes. One electrode 22 is made of wire mesh so that the high-energy photon can shine through the mesh and excite the gas molecules when they pass in front of the UV window 19. FIG. 4 shows a sectional view of the geometry of the PID along the line 3—3 of FIG. 1. As shown, the electrode 22 is made of wire mesh. In contrast, the other electrode 23 need not be made of wire mesh as shown in FIG. 3, a sectional view of the PID along the line 2—2 of FIG. 1. In FIGS. 1 and 2, the exhaust gas is let out of the chamber through a gas outlet 28. The ions collected on the electrode 22 is measured by an electrometer 29.

As described above, it is desirable in many instances to be able to detect and measure different types of volatile gases that may exist. In accordance with another embodiment of the invention, as shown in FIG. 5, multiple gas discharge lamps 11a, 11b and 11c, with different photon energy, may be used in the same PID instrument. The photon energy of each lamp is determined by the type of gases inside the lamp and the UV windows 14a, 14b, and 14c corresponding to lamps 11a, 11b, and 11c, respectively, which permits different wavelengths of UV light to pass. For example, in FIG. 5, the first lamp, 11a, has photon energy of 9.8 eV. The second lamp, 11b, has photon energy of 10.2 eV, and the third lamp, 11c, has 11.7 eV photon energy. These lamps are arranged in tandem to measure a given gas stream as it passes through the ionization chambers in front of each lamp. The separation between corresponding electrode pairs (22a and 23a, 22b and 23b, 22c and 23c) is between 0.020 and 0.040 inch, inclusive. Individual mesh electrodes 22a, 22b, 22c are associated with electrodes 23a, 23b, 23c. In the example shown in FIG. 5, an electrometer 29a, 29b, 29c is associated with each pair of electrodes. As a result, the ion current associated with each lamp is measured and can be used to detect and determine the concentration of a corresponding gas. The UV discharge lamp can be turned on and off very rapidly. The new chamber design will also allow the PID to have instantaneous response to the photo-ionization process. Therefore, it is no longer necessary to keep the lamp on continuously. In this invention, the lamp is turned on long enough for the light output to be stabilized and the measurement taken. It is then turned off until next time for another measurement. The energy consumption of the lamp is greatly reduced. For example, in a typical application of PID instrument, the gas sample is usually measured at 1 second interval. Since it only takes about 100 ms to turn on the lamp and do the measurement, the actual "on" time for the lamp is only 1/10 of a second. Therefore, the total energy consumption for the new PID will be 10 times less than that of a conventional PID instrument.

The current can be measured during both the "on" period and "off" period of the lamp. Since there is no photo-ionization process during the "off" period, the measurement obtained during the "off" period is most likely due to other system noise or leakage current caused by moisture in the gas stream. By subtracting the "off" period measurement from the "on" period measurement, it is possible to eliminate some of the system errors and improve measurement accuracy.

This invention was incorporated in a miniaturized portable PID instrument. Referring to FIG. 1, the lamp 11 was made of a glass tube, 0.5" in diameter and 1.8" in length. The glass tube was filled with helium and argon gases. Two copper plates of 0.5" by 1.5" were used as the electrodes 17, 18. An AC high-voltage source (1000 V peak to peak, 30 kHz) was connected to the electrodes. The resulting gas discharge glow and the UV light radiated through the UV windows at the end of the glass tube. The ionization chamber included two steel electrodes with a Teflon spacer (0.020" thick) between them. A DC voltage of 150 V was applied between the electrodes 22, 23. The instrument was sensitive to a gas level below 1 ppm.

What is claimed:

1. A photo-ionization detector for detecting volatile gases comprising a flat, elongated ionization chamber including spaced major surfaces, at least one of said major surfaces being transparent to photons, a plurality of pairs of spaced, flat electrodes adjacent said major surfaces along the length of the ionization chamber, the electrodes adjacent said at least one transparent major surface having an open configuration to allow photons to travel into the space between electrodes, a plurality of UV light sources adjacent said at least one transparent major surface along the length of the ionization chamber adjacent said electrodes having an open configuration, said light sources selected to emit photons of different energies, means for applying a voltage between said electrodes, and means for measuring the current flow between pairs of electrodes resulting from ionization of gases flowing therebetween.

2. A photo-ionization detector for detecting and measuring the concentration of gases comprising:

an ionization chamber including a plurality of surfaces to form a volume of space wherein at least one of the surfaces is transparent to particles emitted by an ionizer;

means for introducing, moving, and removing gases in the ionization chamber;

an ionizer including an ionizer window, the ionizer window positioned adjacent to the ionization chamber, wherein the ionizer emits particles of predetermined energy to form ions in the ionization chamber;

a plurality of electrodes placed within the ionization chamber, wherein the electrode positioned closest to the ionizer window is made of wire mesh to allow particles to pass through the electrode;

means for establishing and maintaining an electric potential between the electrodes; and means for measuring the current flow in the electrodes, the current flow generated from the ionized gas molecules contacting an electrode.

3. A photo-ionization detector of claim 2 wherein the ionization chamber has an elongated volume.

4. A photo-ionization detector of claim 2 wherein at least one pair of surfaces are opposing.

5. A photo-ionization detector of claim 4 wherein the opposing surfaces are parallel.

6. A photo-ionization detector of claim 4 wherein the shape of the volume of space is relatively flat.

7. A photo-ionization detector of claim 4 wherein the electrodes are positioned sufficiently adjacent to the opposing walls such that a substantial amount of the gases in the ionization chamber is moving between the electrodes.

8. A photo-ionization detector of claim 5 wherein the ionizer is an ultraviolet lamp.

9. A photo-ionization detector of claim 2 wherein the particles emitted from the ionizer are photons.

10. A photo-ionization detector of claim 2 comprising a plurality of ionizers wherein each ionizer emits particles of predetermined energy that is different from the predetermined energies associated with particles emitted from other ionizers, each ionizer emits particles of predetermined energy toward a pair of electrodes, and each pair of electrodes are connected to a separate means for measuring current flow in the electrodes.

11. A photo-ionization detector for detecting volatile organic gases comprising:

an ionization chamber, wherein the ionization chamber includes spaced flat surfaces, and said electrodes are flat and adjacent said flat surfaces with at least one of said flat ionization chamber surfaces being transparent to photons and an adjacent electrode being a mesh to pass photons into the space between the electrodes to ionize the volatile gases between said electrodes, means for causing volatile gases to flow through said ionization chamber, a pair of parallel electrodes disposed in said ionization chamber means for applying a voltage between said electrodes, a UV light source including a UV window, said UV light source positioned adjacent said ionization chamber for injecting photons of predetermined energy into said ionization chamber whereby said photons ionize gases flowing through said ionization chamber between said electrodes, and means for measuring the current flow between said spaced electrodes resulting from ionization of the volatile gases flowing through the ionization chamber between the electrodes.

12. A photo-ionization detector as in claim 11 wherein the electrodes are spaced between 0.020 and 0.040 inches.

13. A photo-ionization detector for detecting and measuring the concentration of gases comprising:

an ionization chamber including a plurality of surfaces to form a relatively flat volume of space wherein at least one of the surfaces is transparent to particles emitted by an ionizer, wherein at least one pair of surfaces is opposing;

means for introducing, moving, and removing gases in the ionization chamber;

an ionizer including an ionizer window, the ionizer window positioned adjacent to the ionization chamber, wherein the ionizer emits particles of predetermined energy to form ions in the ionization chamber;

a plurality of electrodes placed within the ionization chamber, the electrodes spaced at most 0.040 inch from each other;

means for establishing and maintaining an electric potential between the electrodes; and means for measuring the current flow in the electrodes, the current flow generated from the ionized gas molecules contacting an electrode.

14. A photo-ionization detector for detecting and measuring the concentration of gases comprising:

an ionization chamber including a plurality of surfaces to form a volume of space wherein at least one of the surfaces is transparent to particles emitted by an ionizer;

means for introducing, moving, and removing gases in the ionization chamber;

a plurality of ionizers including an ionizer window, the ionizer window positioned adjacent to the ionization chamber, wherein each ionizer emits particles of predetermined energy to form ions in the ionization chamber, wherein each ionizer emits particles of predetermined energy that is different from the predetermined energies associated with particles emitted from other ionizers, each ionizer emits particles of predetermined energy toward a pair of electrodes, and each pair of electrodes are connected to a separate means for measuring current flow in the electrodes;

a plurality of electrodes placed within the ionization chamber;

means for establishing and maintaining an electric potential between the electrodes; and means for measuring the current flow in the electrodes, the current flow generated from the ionized gas molecules contacting an electrode.

* * * * *